(12) United States Patent
Iacobucci et al.

(10) Patent No.: US 7,071,347 B2
(45) Date of Patent: Jul. 4, 2006

(54) BENZOFURANONE STABILIZATION OF PHOSPHATE ESTERS

(75) Inventors: Paul Albert Iacobucci, Hilversum (NL); Anantha Desikan, Peekskill, NY (US); Alan Abramson, Mobile, AL (US)

(73) Assignee: Supresta LLC, Ardsley Park, NY (US)

( * ) Notice: Subject to any disclaimer, the term of this patent is extended or adjusted under 35 U.S.C. 154(b) by 0 days.

(21) Appl. No.: 10/220,408

(22) PCT Filed: Mar. 1, 2001

(86) PCT No.: PCT/US01/06674

§ 371 (c)(1),
(2), (4) Date: Jan. 15, 2003

(87) PCT Pub. No.: WO01/66552

PCT Pub. Date: Sep. 13, 2001

(65) Prior Publication Data

US 2006/0063947 A1   Mar. 23, 2006

Related U.S. Application Data

(60) Provisional application No. 60/186,882, filed on Mar. 3, 2000.

(51) Int. Cl.
*C07F 9/02* (2006.01)

(52) U.S. Cl. .................................................... 558/150

(58) Field of Classification Search ................. 558/150
See application file for complete search history.

(56) References Cited

U.S. PATENT DOCUMENTS

| | | | |
|---|---|---|---|
| 1,958,210 A | 5/1934 | Winfield | 260/99.2 |
| 2,113,951 A | 4/1938 | Royal | 260/154 |
| 3,681,482 A | 8/1972 | Patel et al. | 260/989 |
| 3,852,288 A | 12/1974 | Baum et al. | 260/247.7 D |
| 3,931,360 A | 1/1976 | Giolito | 260/975 |
| 3,931,361 A | 1/1976 | Jaffee et al. | 260/975 |
| 3,931,362 A | 1/1976 | Giolito et al. | 260/975 |
| 3,931,363 A | 1/1976 | Giolito et al. | 260/975 |
| 3,931,364 A | 1/1976 | Giolito et al. | 260/975 |
| 3,931,365 A | 1/1976 | Giolito et al. | 260/975 |
| 3,931,366 A | 1/1976 | Giolito et al. | 260/975 |
| 3,931,367 A | 1/1976 | Giolito et al. | 260/975 |
| 4,263,232 A | 4/1981 | Parekh | 260/989 |
| 5,308,899 A | 5/1994 | Michaelis | 524/109 |
| 5,422,415 A | 6/1995 | Michaelis | 128/85 |
| 5,516,920 A | 5/1996 | Nesvadba et al. | 549/307 |
| 5,869,565 A | 2/1999 | Clauss | 524/590 |

OTHER PUBLICATIONS

J. Kenny, "Further Use of Lactone Chemistry to Improve the Performance Cost Profile of Traditional Antioxidant Stabilization Systems", Polymers & Polymer Composites, vol. 8, No. 1, 2000, pp. 37-50.

Technical Briefs: "New Developments in Lactone-Based Stabilizers", Additives for Polymers, 2000, Elsevier Science, pp. 8-10.

*Primary Examiner*—Johann Richter
*Assistant Examiner*—Ebenezer Sackey
(74) *Attorney, Agent, or Firm*—Dilworth & Barrese, LLP

(57) ABSTRACT

A method for decolorizing and stabilizing alkylphenyl esters of phosphoric acid which comprises contacting the esters with an effective amount of a benzofuranone (e.g., is 5,7-di-t-butyl-3-(3,4 di-methylphenyl)3H-benzofuran-2-one) for a sufficient length of time to decolorize and stabilize the esters against subsequent color formation.

7 Claims, No Drawings

US 7,071,347 B2

BENZOFURANONE STABILIZATION OF PHOSPHATE ESTERS

This is a national stage filing of PCT International Patent Application No. PCT/US01/06674, filed Mar. 1, 2001, which claims priority from U.S. Provisional Patent Application Serial No. 60/186,882, filed Mar. 3, 2000.

BACKGROUND OF THE INVENTION

Alkylphenyl esters of phosphoric acid find extensive use as plasticizers for nitrocellulose and polyvinyl chloride (PVC) compositions. In addition, they also serve as additives for gasoline, functional fluids, oils, and are useful as flame retardants in plastics, and the like.

The preparation of alkylphenyl esters of phosphoric acid is generally accomplished by the addition of phosphorus oxychloride, ($POCl_3$) to selected phenols, such as cresols, xylenols, and the like, and gradually heating the resulting reaction mixture to about 180° C. The reaction is accelerated by the presence of a Friedel-Crafts catalyst such as aluminum trichloride ($AlCl_3$). In conventional processing, the reaction product is vacuum distilled to remove unreacted phenols as an initial fraction, and the alkylphenyl phosphate ester as a product fraction, leaving high boiling point materials and the catalyst in the residue. The distilled product fraction is then washed thoroughly with sodium hydroxide solution to remove free phenol and acidic materials, followed by water washing. The product fraction is then generally treated with activated carbon to remove color causing impurities.

This process, which works very well with esters produced from conventional by-product alkylphenols, produces unsatisfactory material when applied to mixed alkylphenols produced by the alkylation of phenol with olefins. It is found that the products discolor upon exposure to air, exposure to heat, or storage in the dark. The discoloration has been attributed to the presence of di(o-alkyl)phenols in the alkylated phenol. Steric hindrance caused by the double ortho substitution in 2,6-dialkylphenols and in 2,4,6-trialkylphenols renders the phenols unresponsive to washing with sodium hydroxide solution, so that they are not removed by the caustic wash.

These so-called "hindered phenols," can oxidize in the presence of air to form highly colored quinones, which are the source of undesirable discoloration in the product. These quinones can bleach somewhat in the light, however, color will reappear upon storage in the dark. The color can intensify when the ester is mixed or milled with polyvinyl chloride (PVC) under the influence of air and heat.

Thus, for example, in the case of 2,6-diisopropylphenol, the corresponding diphenoquinone or benzoquinone is highly colored. Esters made from mixtures of alkylated phenols which contain di-orthoalkylphenols such as 2,6-diisopropylphenol can be too highly colored for many uses, particularly for use as plasticizers. High color phosphate esters have limited utility for plasticizer use and are less marketable.

Color formation in phosphate esters is discussed in U.S. Pat. No. 3,681,482, which correlates the degree of color formation in phosphate esters to the degree of alkyl substitution of the aryl ring. Accordingly, tris(methylphenyl) phosphate will produce less color than tris (dimethylphenyl) phosphate. This may be explained by the fact that the tris (methylphenyl) phosphate has only one methyl group substituted on the aryl ring, whereas tris (dimethylphenyl) phosphate has two methyl groups substituted on the aryl ring and, therefore, has more color.

A number of proposals have been made for methods to overcome the problem of undesirable color formation. For example, U.S. Pat. No. 1,958,210 discloses the use of activated carbon to decolorize and remove oxidizable impurities from phosphate esters. This approach is unsatisfactory because activated carbon is not an effective decolorizing agent for alkylphenyl phosphate esters. In certain instances, for example, in the decolorization of isopropylphenyl diphenyl phosphate ester, the use of activated carbon may increase color formation.

U.S. Pat. No. 2,113,951 discloses a method wherein an alkylphenol such as cresylic acid is distilled in the presence of a mineral acid such as sulfuric, hydrochloric or phosphoric acid, to purify it. The purified cresylic acid is then employed in the manufacture of tricresyl phosphate esters which are supposed to be more stable to the action of heat and light than the corresponding ester made from alkylphenols distilled in the absence of an inorganic acid. The disadvantage of this process is that the phenolic residues oxidize to colored quinones, and must be thoroughly distilled in order to remove them and avoid further color formation.

Another method for reducing color is proposed in U.S. Pat. No. 3,681,482 wherein sodium borohydride is used to permanently bleach and color stabilize tris (alkylphenyl) phosphate esters containing 2,6-diisopropylphenol and the corresponding diphenoquinone. The sodium borohydride reduces the diphenoquinone to the colorless 2,6-diisopropylphenol which, however, remains in the product and is a potential source of discoloration if the product is exposed to oxidizing conditions. Sodium borohydride treatment is also expensive in cost of materials and time, as several hours to overnight treating times are necessary.

Thus, it can be seen that the above methods proposed in the prior art, are not commercially effective for removing color from alkylphenol esters of phosphoric acid, or do not improve the PVC mill stability when these esters are used as PVC plasticizers.

Other attempts to solve this problem have employed a number of other substances as additives for the decolorization of such a composition. Examples of additives include: hydrazines (U.S. Pat. No. 3,852,288); soluble nitrilotriacetate salts (U.S. Pat. No. 3,931,360); certain sodium salts (U.S. Pat. No. 3,931,361); oxidizable nitrogenous compounds (U.S. Pat. No. 3,931,362); triorganoaluminum compounds and their hydrides (U.S. Pat. No. 3,931,363); phosphite esters (U.S. Pat. No. 3,931,364); a water soluble salt of a reduced form of sulfur (U.S. Pat. No. 3,931,365); phosphorus trichloride, in an in-situ addition mode (U.S. Pat. No. 3,931,366); stannous fatty acid salt (U.S. Pat. No. 3,931,367); and oxygenated thiourea (U.S. Pat. No. 4,263,232).

SUMMARY OF THE PRESENT INVENTION

This invention relates to the stabilization and decolorization of phosphate esters using a benzofuranone additive for such a result.

DESCRIPTION OF THE PREFERRED EMBODIMENTS

Permanent removal of color from colored phosphate esters according to the method of this invention is achieved by contacting the phosphate ester with an effective amount of a benzofuranone additive for a time sufficient to decolorize the phosphate ester to the desired level, and stabilize it against subsequent color formation. The preferred benzofuranone additive for use herein is 5,7-di-t-butyl-3-(3,4 di-methylphenyl)3H-benzofuran-2-one which has a CAS Number of 181314-48-7. It is commercially available from Ciba Additives under the trademark "HP-136".

This invention is applicable to all phosphate esters which are made from alkylated phenol mixtures which contain hindered phenols, e.g., phenols containing alkyl groups on both positions ortho to the hydroxyl group. The esters may contain 0.5 to 3 alkylaryl groups and 0 to 2.5 phenyl groups.

Preferably, the triaryl phosphate esters treated by the process of this invention are a mixture of esters containing 1 to 2 alkaryl groups. The esters correspond to the general formula:

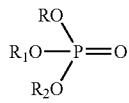

where R is alkylaryl and $R_1$ and $R_2$ may be alkyl, alkaryl, aralkyl, or aryl, and wherein the alkyl groups can contain from 1–20 carbon atoms, more preferably from 1 to 12 carbon atoms. Some triphenyl phosphate may also be present. The alkylated phenols which contain hindered phenols are usually made by alkylating phenol with $C_1$–$C_{12}$ unsaturated hydrocarbons such as ethylene, propylene, isobutylene and its isomers, amylene and its isomers, tripropylene, tetrapropylene, decene, dodecene, diisobutylene and the like. Typical examples of alkyl radicals are as follows: methyl, ethyl, normal propyl, isopropyl, normal butyl, isobutyl, secondary butyl, tertiary butyl, normal amyl, isoamyl, 2-methylbutyl, 2,2-dimethyl propyl, 1-methyl butyl, diethylmethyl, 1,2-dimethyl propyl, tertiary amyl, normal hexyl, 1-methylamyl, 1-ethyl butyl, 1,2,2-trimethyl propyl, 3,3-dimethyl butyl, 1,1,2-trimethyl propyl, 2-methyl amyl, 1,1-dimethyl butyl, 1-ethyl 2-methyl propyl, 1,3-dimethyl butyl, isohexyl, 3-methylamyl, 1,2-dimethyl butyl, 1-methyl 1-ethyl propyl, 2-ethyl, normal heptyl, 1,1,2,3-tetramethyl propyl, 1,2-dimethyl 1-ethyl propyl, 1,1,2-trimethyl butyl, 1-isopropyl 2-methyl propyl, 1-methyl 2-ethyl butyl, 1,1-diethyl propyl, 2-methyl hexyl, 1,1-dimethyl amyl, 1-isopropyl butyl, 1-ethyl 3-methyl butyl, 1,4-dimethyl amyl, isoheptyl, 1-methyl 1-ethyl butyl, 1-ethyl 2-methyl butyl, 1-methyl hexyl, 1-1-propyl butyl, normal octyl, 1-methyl heptyl, 1,1-diethyl 2-methyl propyl, 1,1,3,3-tetramethyl butyl, 1,1-diethyl butyl, 1,1-dimethyl hexyl, 1-methyl 1-ethyl amyl, 1-methyl 1-propyl butyl, 2-ethyl hexyl, 6-methyl heptyl, normal nonyl, 1-methyl octyl, 1-ethyl heptyl, 1,1-dimethyl heptyl, 1-ethyl 1-propyl butyl, 1,1-diethyl 3-methyl butyl, diisobutyl methyl 3,5,5-trimethyl hexyl, 3,51dimethyl heptyl, normal decyl, 1-propyl heptyl, 1,1-diethyl hexyl, 1,1-dipropyl butyl, 2-isopropyl 5-methyl hexyl and $C_{11}$–$C_{20}$ alkyl groups. Also included are aralkyl groups, e.g., benzyl, alpha- or beta-phenylethyl, alpha, alpha dimethylbenzyl and the like. Also included are cyclohexyl, cycloheptyl, cyclododecyl, and the like. Typical examples of aryl and alkaryl radicals are phenyl, cresyl, xylyl, alkoxylated phenyl, isopropylphenyl, butylphenyl, alpha-alkylbenzylphenyl and alpha, alphadialkylbenzylphenyl, e.g., alpha-methylbenzylphenyl, alpha, alpha dimethylbenzyl phenyl, tert-nonylphenyl amylphenyl, tert-butylphenyl, isooctylphenyl, dodecylphenyl, tertiary octylphenyl and the like.

The invention can be further exemplified by first showing the preparation of an ester via the alkylation of phenol with an olefin, followed by addition of POCl$_3$. These alkylated phenols produce esters which are similar to those produced with conventional by-product coal tar cresylic acids or methylphenols. The esters are generally made by reacting an alkylphenol with POCl$_3$ in the presence of a Friedel-Crafts catalyst at an elevated temperature, typically about 180° C., until the reaction is complete, as noted by the cessation of HCL evolution. The reaction mixture is then heated to distill excess phenols overhead. The temperature and/or vacuum is then increased and the phosphate ester product is distilled leaving the catalyst and a small amount of high boiling distillation residue.

Conventionally, the ester product is washed with aqueous alkali to remove free phenols which are generally present in the range of about a few tenths of a percent. The washed product is separated from the water and generally treated with activated carbon and a filter aid, such as diatomaceous earth, and filtered. However, product discoloration caused by hindered phenols in the presence of air and heat can ensue, rendering the product unsuitable for use in applications where lack of color is important. In accordance with this invention, the phosphate ester product is treated for color removal and color stabilization by contacting the finished product alkylphenol phosphate ester with an effective amount of a benzofuranone additive, as previously described, until the color is adequately reduced. U.S. Pat. No. 5,516,920, entitled "3-Arylbenzofuranones", is incorporated herein in its entirety for the description of the type of benzofuranone additives that can be used in accordance with the present inventiuon.

Treatment times will vary, generally from about five minutes to about twenty-four hours, depending upon the amount of phosphate ester treated, the amount and concentration of the benzofuranone additive that is selected for use, the temperature, agitation, and the like. Preferably, the phosphate esters are washed for about one hour to about five hours at a temperature of about 20° C. to about 100° C. More preferably, the treatment is carried out at temperatures of about 45° C. to about 70° C.

The amount of benzofuranone that is used can vary in amount from about 1 ppm to about 2%, by weight of the phosphate ester treated. Larger amounts of the benzofuranone can be employed, but no advantage is accrued thereby. It is preferred to use an amount ranging from about 5 ppm to about 0.1% by weight of the phosphate ester. The particular amount of soluble benzofuranone employed in any given instance will to some extent be influenced by a number of factors, which include the amount of color present, the extent of color improvement desired, the particular phosphate ester treated, treatment time, and the like.

The method of this invention is generally conducted under atmospheric pressure. However, higher or lower pressures may be used. It may also be conducted under an inert atmosphere, such as nitrogen which may serve to repress re-oxidation.

The method of this invention may be carried out batchwise or in a continuous manner.

One particular advantage of the instant invention is that after treatment of the phosphate ester with the benzofuranone additive, no additional steps or special treatment other than an optional washing step, phase separation and drying may be needed. Trace residual benzofuranone, if present, does not appear to have an adverse effect on the commercial properties of the phosphate esters.

The following Examples are illustrative of the methods disclosed above, and are provided without any intention that the invention be limited thereto. In the examples and throughout the specification, all parts and percentages are by weight, unless otherwise noted.

EXAMPLE 1

In this Example a phosphate ester sample (PHOSFLEX 31L) was treated with varying amounts of the lactone based stablizer (HP 136) to determine the color stability of the material. Accelerated color stability measurements were done at 80° C. for twenty-eight hours in a closed sample bottle. Results of this test are summarized in Table 2. It is clear from this measurement that in the concentration range 10–50 ppm (by weight), the stabilizer is effective in decolorizing and stabilizing the phosphate ester sample. The sample without the additive tested under the same conditions developed significant color—APHA of over 300. The starting color for this sample was about 50 APHA.

TABLE 2

Results of the stability tests in the additive concentration range 10–50 ppm. Tests were done at 80° C. for 28 hours.

| Additive Amount (ppm) | Color At End of Test (APHA) |
|---|---|
| 0 | 361 |
| 10 | 27 |
| 30 | 19 |
| 50 | 21 |

EXAMPLE 2

In this Example a phosphate ester sample (PHOSPHLEX 21L) was treated with varying amounts of the lactone based stabilizer (HP 136) to determine the color stability of the material. Accelerated color stability measurements were done at 80° C. for twenty-eight hours in a closed sample bottle. Results of this test are summarized in Table 2. It is clear from this measurement that in the concentration range 10–50 ppm (by weight), the stabilizer is effective in decolorizing and stabilizing the phosphate ester sample. The sample without the additive tested under the same conditions developed significant color: APHA of over 300. The starting color for this sample was about 50 APHA.

TABLE 3

Results of the stability tests in the additive concentration range 10–50 ppm (by weight). Tests were done at 80° C. for 28 hours.

| Additive Amount (ppm) | Color At End of Test (APHA) |
|---|---|
| 0 | 327 |
| 10 | 21 |
| 50 | 21 |

EXAMPLE 3

In this Example a phosphate ester sample (PHOSFLEX 21L) was treated with the lactone based stabilizer (HP 136) at levels of about 100 ppm to determine the color reduction efficiency and stability of the material. Accelerated color stability measurements were done at 80° C. for twenty-eight hours in a closed sample bottle. At this level of stabilizer, the color of the sample was reduced from about 200 APHA to about 25 APHA. The material was stable at this color level for an extended period of time at the described test conditions. This clearly demonstrated that the lactone additive was efficient in both reducing the color and in stabilizing the material against color formation.

We claim:

1. A method for decolorizing alkylphenyl esters of phosphoric acid which comprises contacting said esters with an effective amount of 5,7-di-t-butyl-3-(3,4 di-methylphenyl) 3H-benzofuran-2-one for a period of time sufficient to reduce the color to the desired level whereby said esters are decolorized and stabilized against subsequent color formation.

2. The method of claim 1 wherein said alkylphenyl esters correspond to the formula:

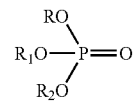

wherein R is alkaryl and $R_1$ and $R_2$ are selected from the group consisting of alkyl, aralkyl, alkaryl and aryl, and wherein the alkyl groups contain from about 1 to about 20 carbon atoms.

3. The method of claim 2 wherein said alkyl groups contain from 1 to about 12 carbon atoms.

4. The method of claim 1 wherein the alkylphenyl esters contain unreacted substituted and unsubstituted phenols.

5. The method of claim 2 wherein said decolorizing and stabilizing is conducted under an inert atmosphere.

6. The method of claim 5 wherein said inert atmosphere comprises nitrogen.

7. The method of claim 1 wherein the alkyl phenyl ester of phosphoric acid is an isopropylphenyl phenyl phosphate.

* * * * *